United States Patent
Wang et al.

(10) Patent No.: US 7,906,459 B2
(45) Date of Patent: Mar. 15, 2011

(54) STABLE AND WATER-SOLUBLE PLANT GROWTH REGULATOR LIQUID COMPOSITIONS AND METHODS FOR USE OF SAME

(75) Inventors: Yueh Wang, Arlington Heights, IL (US); Mark Beach, Bristol, WI (US); Bruce Kirkpatrick, Mundelein, IL (US); Gregory Clarke, Dillsburg, PA (US); John Lopez, Gurnee, IL (US); Prem Warrior, Green Oaks, IL (US); Bruce Baldi, Libertyville, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 5 days.

(21) Appl. No.: 12/565,943

(22) Filed: Sep. 24, 2009

(65) Prior Publication Data
US 2010/0016165 A1    Jan. 21, 2010

Related U.S. Application Data

(63) Continuation of application No. 11/597,149, filed as application No. PCT/US2005/017909 on May 23, 2005.

(60) Provisional application No. 60/574,354, filed on May 24, 2004.

(51) Int. Cl.
*A01N 43/40* (2006.01)
*A01N 3/02* (2006.01)
*A01N 25/00* (2006.01)
*A01N 63/00* (2006.01)
*C01B 11/06* (2006.01)
*A61K 8/365* (2006.01)
*A61Q 11/00* (2006.01)

(52) U.S. Cl. ............ 504/130; 504/113; 504/116.1; 504/118; 252/187.27; 424/55

(58) Field of Classification Search ............ 504/113, 504/116.1, 118, 130; 252/187.27; 424/55
See application file for complete search history.

(56) References Cited

U.S. PATENT DOCUMENTS

| 5,198,254 | A | * | 3/1993 | Nisperos-Carriedo et al. ............ 426/102 |
| 5,877,112 | A | * | 3/1999 | Roberts et al. ............ 504/206 |
| 6,509,297 | B1 | | 1/2003 | Coleman |
| 6,569,809 | B1 | | 5/2003 | Sato et al. |
| 2003/0050194 | A1 | | 3/2003 | Hopkinson et al. |
| 2004/0053788 | A1 | * | 3/2004 | Hayashi et al. ............ 504/363 |
| 2008/0039322 | A1 | | 2/2008 | Wang et al. |
| 2008/0213326 | A1 | | 9/2008 | Amrhein et al. |
| 2009/0163449 | A1 | | 6/2009 | Wempe |
| 2010/0099567 | A1 | | 4/2010 | Shinichi |

FOREIGN PATENT DOCUMENTS

CN    1548132 A    11/2004

OTHER PUBLICATIONS

Lownds, N. K., Effect of oxyethylene chain length on ethylene production by cowpea of mung bean and comparison with linear alcohol hydrophobes, Plant Growth Regulation 11, 1992, pp. 139-145.*

* cited by examiner

*Primary Examiner* — Fereydoun G Sajjadi
*Assistant Examiner* — Danielle Sullivan
(74) *Attorney, Agent, or Firm* — Wood, Phillips, Katz, Clark & Mortimer

(57) ABSTRACT

Soluble and stable liquid compositions containing a plant growth regulator selected from the group consisting of cytokinin and a gibberellin, an acid solubilizer such as citric acid, tartaric acid or glycolic acid and a solvent; as well as methods for making and using the composition are disclosed. The compositions improve solubility, handling, stability, safety, as well as activity improvements such as improved plant growth, yield, fruit thinning or sizing and quality. The compositions are soluble and stable by adding an ethoxylated alkyl alcohol wherein the growth regulator is 6-benzyladenine (6-BA) or forchlorfenuron (CPPU) and the ethoxylated alcohol surfactant is $C_{12-15}$ alkyl alcohol in propylene glycol. The compositions may also contain a cytokinin such as 6-benzyladenine (6-BA) or forchlorfenuron (CPPU) that is increased in solubility and activity and by synergistically combined with $GA_3$ or $GA_4A_7$ as well as in storage stability by adding an antioxidant. The compositions are formulated in a ready-to-mix formulation.

6 Claims, 1 Drawing Sheet

STABLE AND WATER-SOLUBLE PLANT GROWTH REGULATOR LIQUID COMPOSITIONS AND METHODS FOR USE OF SAME

CROSS-REFERENCE TO RELATED APPLICATION

This application is a continuation application of Ser. No. 11/597,149, filed Oct. 26, 2007, which claims priority of PCT/US2005/017909 filed May 23, 2005, which claims priority to provisional application Ser. No. 60/574,354, filed May 24, 2004.

FIELD OF THE INVENTION

The present invention is directed to soluble and stable liquid compositions including at least one plant growth regulator, at least one acid solubilizer, at least one surfactant adjuvant, and at least one solvent; as well as methods for making and using the compositions. The soluble liquid composition advantageously improves the preparation, the storage stability, the handler safety and the performance of a plant growth regulator formulation for spray application, as such composition is highly soluble in use dilutions, is easily metered, can be more highly concentrated and is dust-free. A presently preferred soluble liquid composition includes at least one plant growth regulator selected from the group consisting of an adenine cytokinin, an acid solubilizer selected from the group consisting of citric acid, tartaric acid and glycolic acid, a dilution solubilizer comprising a nonionic and/or anionic surfactant blend and a solvent comprising propylene glycol. The growth regular is preferably 6-benzyladenine (6-BA).

The present invention is also directed to soluble and stable liquid compositions comprising at least one plant growth regulator selected from the group consisting of a phenylurea cytokinin, a dilution solubilizer comprising nonionic and/or anionic surfactant blend and a solvent comprising propylene glycol. The growth regulator is preferably forchlorfenuron (CPPU) and the nonionic surfactant is preferably ethoxylated $C_{12-15}$ alkyl alcohols.

The present invention is also directed to obtaining a synergistic effect by combining cytokinin and gibberellin plant growth regulators such as 6-BA and/or CPPU with $GA_3$ or $GA_4A_7$.

BACKGROUND OF THE INVENTION

Plant growth regulators are useful for influencing a range of plant developmental processes including stem elongation, germination, dormancy, flowering, sex expression, enzyme induction, fruit size and quality, as well as leaf and fruit senescence. Plant growth regulators may be formulated in at least five different types of formulations: 1) solutions, 2) wettable powders, 3) soluble powders, 4) tablets, and 5) water-soluble or dispersible granules. In order to use such formulations, they must be diluted in an aqueous solution prior to conventional spray application. Each of the conventional types of formulations has disadvantages, so research to provide improved plant growth regulator formulations continues. The disadvantages of the conventional formulations will be discussed with reference to two important plant growth regulator classes, the gibberellins and the cytokinins, as representative of conventional formulations of plant growth regulators in general.

Gibberellins are one class of plant growth regulators which are diterpenoid acids. Gibberellins are commercially produced by fermentation of a natural fungus, *Gibberella fugikuroi*. Gibberellins are marketed under various trade names and are commercially used on a variety of fruit orchards, vegetable crops, row crops, and ornamental crops. The predominantly used gibberellic acid is $GA_3$, formulated in any of the five forms described above. The other commonly used gibberellins are a combination of two, $(GA_{4+7})$ which are primarily formulated as solutions in isopropyl alcohol, tetrahydrofurfuryl alcohol (THFA) or propylene glycol. Due to diterpenoid structure of gibberellins containing double bonds and cyclic lactone, they are less stable in liquid form, especially in water.

Cytokinins are another class of plant growth regulators which are generally defined as N6-substituted adenine derivatives such as trans-zeatin, 6-benzyladenine and kinetin. Recently, a new class of cytokinins has been identified and they possess N-phenylurea substituted structure such as forchlorfenuron (CPPU) and thidiazuron (TDZ). Cytokinins are of extreme importance in regulating plant growth and development, especially cell division. They are marketed under various trade names and are commercially used in fruit thinning and sizing as well as pre- and post-harvest treatments of ornamental plants and flowers. Cytokinins have low solubility in water or solvent and solubility improvement in formulation and in use dilution are important for obtaining their biological effectiveness.

Solution Formulations

Gibberellin and cytokinin solution formulations are disadvantageous in several respects. The solutions, such as those of 6-BA in propylene glycol or THFA, are less concentrated due to low solubility of actives, and GA4+A7 have limited stability due to oxidation or chemical degradation. The result is that current GA4+A7 products have a limited shelf life due to 10-15% loss per year. Overformulation and rework are then required for aged product in order to meet label claim. Of the currently used solvents, isopropyl alcohol and methyl alcohol offer severe disadvantages such as flammability and toxicity, which lead to restrictions in manufacturing, packaging, labeling, transportation, and warehousing of such solutions. A more powerful THFA solvent has to be used in some of the 6-BA formulations, however, THFA is considered corrosive to the eye and skin. Moreover, low solubility of cytokinins in propylene glycol does not permit preparation of high potency solution formulations. These low strength solution formulations also require larger packaging, more storage space, and higher associated transportation, warehousing, and container disposal costs. Due to very low solubility and undesirable hydrolysis, it has not been possible to formulate gibberellins or cytokinins in aqueous systems. Some examples of solution formulations of gibberellins include PROGIBB 4% ®, PROVIDE®, PROCONE®, RALEX®, RELEASE LC® and RYZUP®, cytokinins include ACCEL®, and REGULEX®, and gibberellin and cytokinin combinations include PROMALIN®, all available from Valent BioSciences Corp.

Powder Formulations

A soluble powder formulation is one which, when mixed with water, dissolves readily in water and forms a true solution. Once the solution is formed, no further mixing or agitation of the tank-mix is required. Mixing is a process of combining different materials, usually to a homogeneous state. Agitation aids the process of mixing, and is a mechanical process involving rotating shafts of blades in the bottom of the spray tank.

An example of a powder gibberellin formulation is PROGIBB 2X®, available from Valent BioSciences Corp., which contains 20% by weight of the active ingredient, gibberellin. A wettable powder formulation is a dry, finely ground formulation. In this formulation, the active ingredient is combined with a finely ground dry carrier, usually a mineral clay, along with other ingredients that enhance the ability of the powder to be suspended in water. Upon mixing the wettable powder with water, a suspension is formed, which is then applied by a spray technique. Examples of a wettable powder gibberellin formulation include PROGIBB PLUS®, ACTIVOL 10%® and RELEASE®, all available from Valent BioSciences Corp.

The primary disadvantage of wettable powder and soluble powder formulations is that they tend to produce dust upon handling, such as when pouring, transferring or measuring them. This dust may pose health hazards. Further, powder formulations tend to wet poorly and also solubilize slowly upon addition to water. Powder formulations thus take longer times to wet, disperse and solubilize in the tank-mix. Formation of lumps or partially solubilized spray solutions will lead to uneven distribution of the plant growth regulator in the tank-mix with potential for reduced field performance. Sometimes, foam in the spray tank caused by spray tank adjuvants can also affect wetting and solubility of wettable and soluble powders. Wettable powder formulations will also leave undesirable insoluble residues both in the tank and on the sprayed foliage and fruit. For insoluble cytokinins, the wettable powder formulations of large particle size are ineffective as plant growth regulators.

Tablet Formulations

Tablet formulations are pre-measured dosage delivery systems. They are useful in small areas, or for ornamental purposes. Tablet formulations may be effervescent, which dissolve in water over a period of two to ten minutes depending upon the type and size of the tablet. However, tablets deliver only between 0.1-1 gram of active ingredient per tablet. They are not ideal for large-scale field operations. Moreover, effervescent tablets are highly susceptible to humidity, may be slow to dissolve and are expensive.

Water-Soluble or Dispersible Granules

Water-soluble or water-dispersible granules are also known as soluble or wettable granules. This type of formulation is similar to a wettable powder, except that the active ingredient is formulated as granular particles of 100 to 300 micron size. To prepare the water-soluble or dispersible granules for spray application, they are completely soluble or dispersible in water upon agitation. Many different water-soluble or water-dispersible granular formulations are known for agricultural chemicals. For example, EP 0 252 897 and U.S. Pat. No. 4,936,901 disclose encapsulated plant growth regulators in water dispersible granular formulations, U.S. Pat. No. 6,387,388 B1 and U.S. Patent Application Publication US 2002/0114821 A1 disclose an extruded water-soluble insecticide, and U.S. Pat. No. 5,622,658 discloses an extrudable composition for preparing water-dispersible granules. An example of a granular gibberellin formulation containing 3.1% active ingredient is Gibberellin Kyowa Soluble Powder, available from Kyowa Fermentation Industry of Japan.

Water-soluble or dispersible granules usually have no greater than eight percent moisture content, and form solution or suspensions when added to aqueous solutions. The quality of water-soluble or water-dispersible granules is highly process- and active-ingredient-dependent, and can result in low yield recoveries, poor attrition resistance leading to dust potential, high manufacturing cost and poor dispersion. Generally, sprays of dissolved water-dispersible granular formulations leave undesirable insoluble residues on the treated foliage and fruit.

For plant growth regulators such as gibberellins or cytokinins to be efficacious, the active ingredient must be solubilized in the tank-mixes prior to application. In addition, water-soluble or -dispersible granules can become hardened over time and thus result in poor solubility or dispersibility of the active ingredient. Dust and caking may be problems with certain water-soluble or water-dispersible granules and powder formulations.

Even with liquid formulations, due to poor water and solvent solubility of plant growth regulators such as 6-benzyl adenine and forchlorfenuron (CPPU), THFA is required to be used as a solvent and precipitation or crystallization of active ingredients can occur in field-tank mixing, which will have an adverse effect on the plant growth regulator activity and the handling of a toxic THFA product.

Therefore, a plant growth regulator formulation which provides high potency, product safety, stability and solubility, and avoids the problems associated with conventional formulations, would be advantageous.

BRIEF SUMMARY OF THE INVENTION

Figure 1:
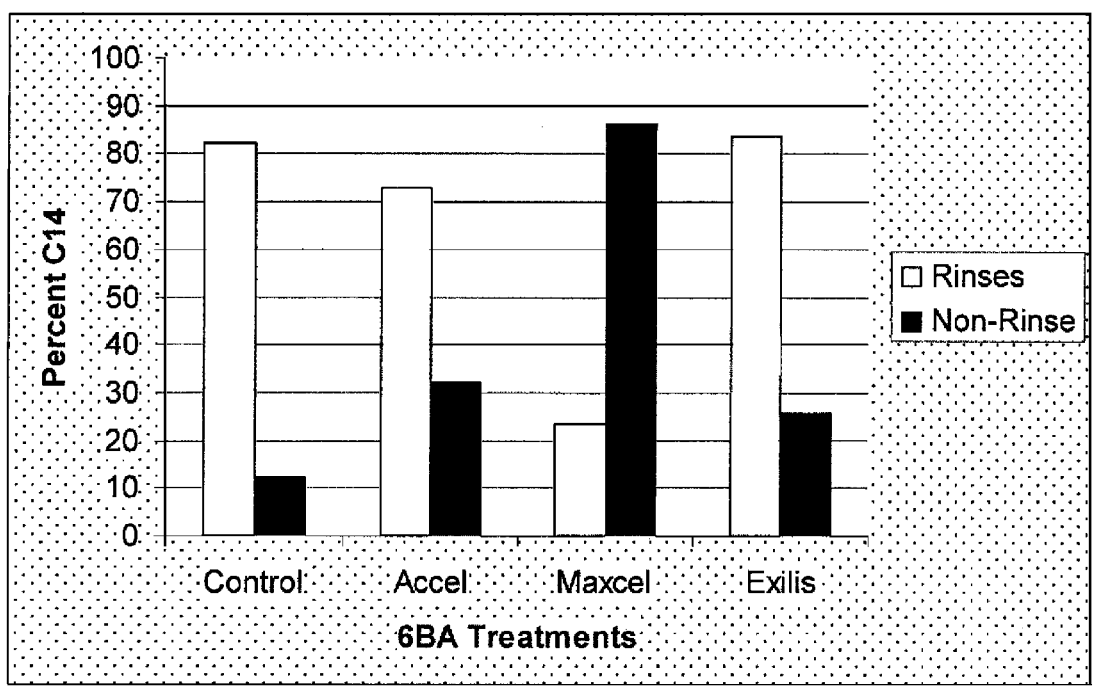
FIG. 1. shows the improved 6-BA uptake of representative compositions of the present invention in comparison with other compositions.

The present invention is directed to a novel plant growth regulator composition in a concentrated liquid form, as well as methods for making and using the composition. The invention improves a plant growth regulator that is normally insoluble such as 6-benzyladenine (6-BA) or forchlorfenuron (CPPU) by making it more soluble, as well as utilizing its synergistic characteristics by combining it with gibberellins such as $GA_3$ and less stable $GA_4A_7$ ($GA_{4+7}$). The composition comprises at least one plant growth regulator and at least one acid solubilizer selected from the group consisting of citric acid, tartaric acid and glycolic acid. The composition preferably includes at least one solvent and one surfactant. The liquid composition advantageously improves handler safety, preparation, penetration and storage stability of a plant growth regulator formulation for spray application, as such composition swiftly dissolves or is highly soluble, is easily metered, can be more highly concentrated and is dust-free for handling. Preferably the plant growth regulator is selected from the group consisting of gibberellins, auxins, cytokinins, organic acids, ethylene biosynthesis inhibitors, and combinations thereof. More preferably, the plant growth regulator is a cytokinin and/or a gibberelin. Most preferably, the plant growth regulator is 6-benzyl adenine or forchlorfenuron (CPPU).

In another embodiment, the composition comprises at least one plant growth regulator and an ethoxylated alkyl alcohol surfactant. The growth regulator is preferably forchlorfenuron (CPPU) and the ethoxylated alkyl alcohol surfactant is a $C_{12-15}$ alcohol in propylene glycol solvent.

Additionally, the composition may further comprise an antioxidant. The antioxidant may be propyl gallate, ethoxyquin, butylated hydroxyanisole, butylated hydroxytoluene, tertiary butylhydroquinone and combinations thereof. The surfactant may be ethyoxylated alcohols, dioctyl sodium sulfosuccinates, ethoxylated fatty acids, ethoxylated vegetable oils, glycol esters, sorbitan fatty acid esters, and ethoxylated sorbitan fatty acid esters and combinations thereof.

The composition may also contain at least one additional component such as a cosolvent (ethyl lactate, butyl lactate, methyl fatty ester or acetyltributyl citrate, all EPA list 4 inerts), a sticker, a spreader sticker, a systemic acquired resistance inducer, an anti-foaming agent, a preservative, a humectant, a dye, a U.V. protectant, a buffer, a carrier or a combination thereof.

The preferred formulation of the composition comprises benzyadenine, anhydrous citric acid, ethoxylated $C_{12-15}$ alcohols, propyl gallate and propylene glycol. The preferred weight range of the formulation is from about 1.5 to about 3.0 weight percent 6-benzyladenine, from about 1.5 to about 3.0 weight percent anhydrous citric acid, from about 3.5 to about 5.5 weight percent ethoxylated $C_{12-15}$ alcohols, from about 0.05 to about 0.20 weight percent propyl gallate and from about 91.00 to about 93.00 weight percent propylene glycol.

The invention is also directed to a method of regulating plant growth comprising the step of treating soil, a seed or a plant with an effective growth-regulating amount of the composition described above. The composition of the present invention may be formulated as a ready-to-mix formulation that is diluted in water and spray-applied in order to improve plant growth, yield, fruit thinning, fruit sizing, flowering and quality. The plant is preferably a fruit bearing plant, as for example one that produces grapes, apples, pears, peaches, cherries, lemons, limes, oranges, pistachio or tangerines.

The invention is also directed to a method of preparing a soluble liquid plant growth regulator formulation comprising the steps of mixing the plant growth regulator, acid solubilizer, surfactant, antioxidant and solvent to produce a final soluble liquid composition. In the method, preparation of the formulation for spray application can be enhanced, since the solubilizer and the surfactant produce clear spray solution of micro- or nano-particle size and prevent the crystallization of insoluble active ingredient in use dilution, and accurate metering and rapid dissolution of the composition can be attained. The formulation of the present invention is high in product solubility, handling safety, storage stability, and improves plant growth, yield, fruit thinning or sizing and quality. The ready-to-mix compositions can be used for liquid insecticide, herbicide and fungicide formulations.

DETAILED DESCRIPTION OF THE INVENTION

We have now surprisingly discovered that highly concentrated, soluble and stable liquid formulations of plant growth regulators are improved if organic acid solubilizers such as citric acid, tartaric acid or glycolic acid are added to the composition and dilution solubility is improved if an ethoxylated alkyl alcohol surfactant is added to the composition. The composition having improved dilution solubility preferably comprises 6-BA or CPPU as the plant growth regulator and propylene glycol as the solvent and the ethoxylated $C_{12-15}$ alcohol as the surfactant. The acid solubilizer prevents crystallization of the active ingredient at ambient or cold storage temperature thereby resulting in a more concentrated liquid formulation. The soluble liquid formulation is still safe, stable and effective.

The phrase "plant growth regulator" as used herein connotes a product which serves to modify the growth and the development of a treated plant to agricultural maturity without killing the plant. Such modification may result from the effect of the material on the physiological processes of the plant, or from the effect of said material on the morphology of the plant. These modifications may also result from any combination or sequence of physiological or morphological factors.

The plant growth regulator may be a gibberellin, an auxin, an organic acid, a cytokinin, an ethylene biosynthesis inhibitor, or a combination thereof. Suitable ethylene biosynthesis inhibitors include aminoethoxyvinylglycine; suitable auxins include indole-3-acetic acid and indole butyric acid; suitable organic acids include a-naphthyl acetic acid and suitable cytokinins include 6-benzyladenine or 6-benzylaminopurine (6-BA), forchlorfenuron (CPPU), thidiazuron (TDZ) and 6-furfurylaminopurine (kinetin).

in the formulation of the present invention, a surfactant may be used as a wetting, solubilizing and penetrating agent for certain plant growth regulators. Suitable surfactants include non-ionic surfactants, anionic surfactants and amphoteric surfactants. Non-ionic surfactants include ethoxylated alkyl alcohols such as TOMADOLS®, ethoxylated vegetable oils such as AGNIQUE SBO® (soybean), CSO (castor) and RSO (rapeseed), ethoxylated sorbitan esters such as EMSORB®, TWEEN®, and T-MAZE®; sorbitan fatty acid esters such as SPAN® and ALKAMUL®; sucrose and glucose esters and derivatives thereof such as MAZON®, RHEOZAN® and GLUCOPON®; ethoxylated alcohols such as TRYCOL®, BRIJ®, ARMIX®, TERGITOL® and PLURAFAC®; ethoxylated alkylphenols such as IGEPAL®, MACOL® and TRITON®; ethoxylated fatty amines such as TRYMEEN® and ETHOMEEN®; ethoxylated fatty acids such as EMEREST®, ALKAMUL® and TRYDET®; ethoxylated fatty esters such as ALKAMUL® and ATLAS G®; fatty acids such as ATLAS G-1556®; glycerol esters such as MAZOL GMO®; glycol esters such as GLYCOL SEG®; lanolin-based derivatives such as AMERCHOL CAB®; methyl esters such as OLEOCAL ME®; monoglycerides and derivatives such as ETHOSPERSE G-26®; propoxylated and ethoxylated fatty acids such as ANTAROX AA-60®; block copolymers of ethylene oxide and propylene oxide such as PLURONIC® or SURFONIC®; silicone-based surfactants such as SILWET®, BREAK-THRU® and mixtures of organosilicon surfactant with non-ionic or ionic surfactants; polysaccharides, copolymers of acrylamide and acrylic acid; and acetylenic diol derivatives such as SURFYNOL 104® or tristyrylphenols such as SOPROPHOR® among others.

A presently preferred nonionic surfactant family is the ethoxylated alkyl alcohols of C9 to C15 chains (TOMADOL 25-7, 1-7 or 91-60). Non-ionic surfactants such as natural ethoxylated alcohols (BRIJ®) and vegetable oils (AGNIQUE®) are presently also preferred. Suitable anionic surfactants include phosphate esters such as EMPHOS® and RHODAFAC®; dialkyl sulfosuccinates such as MONAWET®, N-acyl ED3A chelating surfactant (Hampshire) and N-Acyl Sarcosines (Hamposyl) among others.

The tradenames used above of surfactants often are common to a class or series of surfactants. Therefore, where a tradename is mentioned, any surfactant in the family including that tradename will be suitable.

Other components of the formulation may include additional surface active agents, cosolvent, dyes, U.V. (ultra-violet) protectants, antioxidants, antifoams or other components which facilitate product handling and application.

It is also contemplated that the ready-to-mix compositions of this invention may be used in other active ingredients, such as herbicides, fungicides, insecticides, nematicides, biochemical pesticides, plant produced pesticides (botanicals) or plant nutrients.

A presently preferred composition contains technical grade active ingredient gibberellin. A preferred technical grade active ingredient gibberellin is $GA_3$, since it is the most widely used plant growth regulator for agriculture, although other gibberellins, including but not limited to $GA_4$, or $GA_7$, $GA_4A_7$, and combinations of GA3 or GA4A7 with 6-BA or CPPU.

A presently preferred composition includes from about 1.5 to about 3.0 weight percent 6-benzyladenine, from about 1.5 to about 3.0 weight percent anhydrous citric acid, from about 3.5 to about 5.5 weight percent ethoxylated $C_{12-15}$ alcohols, from about 0.05 to about 0.20 weight percent propyl gallate and from about 91.00 to about 93.00 weight percent propylene glycol.

A presently preferred composition includes from about 0.5 to about 2.0 weight percent CPPU, from about 0.5 to about 2.0 weight percent anhydrous citric acid, from about 1.0 to 3.0 weight percent ethoxylated $C_{12-15}$ alcohols and from about 93.0 to 98.0 weight percent propylene glycol.

The Methods of Use

Gibberellins are known plant growth regulators. For example, U.S. Pat. No. 4,242,120 discloses a non-spray combination of a gibberellin with a low molecular weight carbohydrate such as saccharide, glucose, fructose or maltose to stimulate fructification; and U.S. Pat. No. 5,163,993 discloses a combination of gibberellin and a surfactant for thinning grape clusters.

The formulations described above may be used to regulate plant growth of fruit-producing plants, vegetable-producing plants, row crops, vegetable crops, grasses or trees. The benefits of the use of the formulation vary, according to the type of fruit treated. For example, in grapes, treatment with the formulation can lead to cluster elongation, thinning and larger grapes. In oranges, lemons, limes and tangerines, the formulation can lead to a delay the aging of the rind and reduce disorders such as rind staining, water spotting, sticky or tacky surface, puffy rind or rupture under pressure. In cherries, the formulation may advantageously be used to produce larger, brighter colored and/or firmer fruit.

The formulation is preferably diluted in water and sprayed on the plant or tree to be treated. The spraying may be by conventional ground or aerial application equipment. Spray volumes are variable depending upon the orchard or crop, growth stage and climatic conditions. The range may be 5 gallons to 300 gallons/acre or higher. A presently preferred range is between 100 to 250 gallons per acre by pressurized spray application equipment. To prepare a formulation for application, a tank is half-filled with water, followed by spray addition of adjuvant, and then addition of plant growth regulator, followed by addition of more water and mixing for at least 15 minutes prior to actual spraying.

Alternatively, the formulation may be directly applied to the soil (in which the plant will be grown or is growing) with or without granular fertilizers for the improved growth and maintenance of crops.

Moreover, the formulation may be applied to seeds to achieve the same effect. The seed may be rice or paddy, alfalfa, cotton, sorghum, soybeans, corn or other vegetables, ornamental or turf and pasture grass seed, among others.

The concentration of the plant growth regulator will vary depending upon the type of fruit is to be treated, the peculiarities of the locale, and the desired result. In general, the composition may be applied at a field rate of from about 0.01 to about 1.0 lb per acre; preferably at a rate of from about 0.02 to about 0.5 lbs per acre and most preferably at a rate of from about 0.02 to about 0.2 lb/acre. For example, the field spray rates for apples using 6-BA can be about 38-75 g/100 gallon per acre and for grapes using CPPU can be about 4-8 g/250 gallon per acre.

A single application may be enough, though depending upon the particular fruit and desired results, multiple applications may be made.

As used herein the term "plant" includes fruit-producing plants, vegetable-producing plants, row crops, vegetable crops, grasses and trees.

The fruit may be grapes, cherries, lemons, limes, oranges, grapefruit, strawberries, pineapples, stone fruits, apples, pears, peaches, blueberries, pistachio or tangerines. The row crop may be cotton, soybeans, corn, sugar cane or rice, among others. The vegetable crops may be lettuce, artichokes, celery or peppers among others. The grasses may be Bahaigrass (*Paspalum notatum* Flugge), Bentgrass (*Agrostis* L.), Bermudagrass (*Cynodon dactylon* L.), Carpetgrass (*Axonopus affinis* Chase), Kentucky bluegrass (*Poe pratensis* L.), Canada Blugrass (*Poe compressa* L.), Buffalograss (*Buchloe dactyloides* (Nutt.) Englem.), Fescue grasses (*Festuca*), annual Rye grass (*Lolium* L. *multiflorum* Lam.), perennial Rye grass (*Lolium perenne* L.), Saint augustinegrass (*Stenotaphrum secundatum* Kuntze), Japanese lawngrass (*Zoysia japinica* Steud.), Centipedegrass (*Eremochloa ophiuroides* (Munro) Hacck, other turf grasses for residential or commercial establishments, among others.

The invention will be understood more clearly from the following non-limiting representative examples. Of course, the present invention is not limited to the particular embodiments and modes of operation described herein and it is possible to imagine a number of variations in the details without departing from the scope of this invention.

The examples below are presented to describe preferred embodiments and utilities of the invention and are not meant to limit the invention unless otherwise stated in the claims appended hereto.

Example 1

In 500 liter batch size (523 kg by weight), 480.9 kg of propylene glycol solvent is transferred through a heat exchanger to a mixing tank and the solvent is heated to 40° C.-45° C. While in the mixing tank, 10.1 kg of 6-BA tech powder (98.5% active ingredient), 10.5 kg of citric acid powder and 0.5 kg of propyl gallate powder (TENOX PG®) are added. The mixture is agitated until all of the powders are completely dissolved. 21 kg of ethoxylated $C_{12-15}$ alcohol surfactant (TOMADOL 25-7®) is then added. Everything is mixed for additional 10-20 minutes to complete the formulation.

Example 2

Example 2 demonstrates increased solvent solubility of 6-BA (N-6-benzyladenine) by adding soluble organic acids in propylene glycol, and improved water dilution stability of 6-BA and CPPU (Forchlorfenuron or N-(2-chloro-4-pyridinyl)-N-phenylurea) in formulations with low irritating (skin and eyes) surfactants (alkyl alcohol ethoxylates or/and dioctyl sodium sulfosuccinate) and citric acid solubilizer. Soluble, stable, safe and ready-to-mix formulations were achieved with 6-BA or CPPU and acid/surfactant combinations as shown in Table 1 below.

TABLE 1

Solvent Solubility of 6-BA and CPPU at 20 C.

| 100 g Solvent | Organic Acid | 6-BA | CPPU |
|---|---|---|---|
| Propylene Glycol | — | 1.5 g | — |
| Propylene Glycol | 2 g Citric | 2.4 g | — |
| Propylene Glycol | 2 g Tartaric | 2.5 g | — |
| Propylene Glycol | — | — | 7 g |
| Propylene Carbonate | — | — | 6 g |
| Propylene Glycol-n-Propyl Ether | — | — | 10 g |

Composition, Storage and Dilution Stability of VBC-30001 and ABG-3207 Cytokinin Products

| Ingredients, wt % | VBC-30001 | ABG-3207 | Function |
|---|---|---|---|
| 6-Benzyladenine (98.5%) | 1.93 | — | Active |
| Forchlorfenuron (96.9%) | — | 0.84 | Active |
| Citric acid, anhydrous | 2.0 | 0.5 | Solubilizer |
| Alkyl alcohol ethoxylate | 4.0 | 1.0 | Solubilizer |

TABLE 1-continued

Solvent Solubility of 6-BA and CPPU at 20 C.

| Propyl gallate | 0.1 | — | Antioxidant |
| Propylene glycol | 91.97 | 97.66 | Solvent. |

*VBC-30001 is 1.9% 6-BA Liquid and ABG-3207 is .8% CPPU Liquid.

| Storage Stability | 65-022-VB lot | 51-004-VB lot |
|---|---|---|
| Initial | 1.90% 6-BA | .87% CPPU |
| 12 mo./25 C. | 1.89 | .84 |
| 12 mo/25-40 C. | 1.88 | .89 |

Dilution stability in 342 ppm hard water at ~23 C.

| Formulation | Initial | 24 hr |
|---|---|---|
| VBC-30001 | soluble | soluble |
| 2.5%(450 ppm 6-BA) | (clear) | (clear) |
| ABG-3207 | soluble | soluble |
| 2.5% (200 ppm CPPU) | (light blue) | (light blue). |

*Reported solubility of 6-BA and CPPU in 25 C. water are 60 and 39 ppm, respectively. Complete solubilization or submicron suspension (light blue color) of cytokinin is important for obtaining optimal PGR activity in applications.

Table 1 shows the solvent solubility of 6-benzyl adenine (6-BA) and CPPU (forchlorfenuron or N-(2-choloro-4-pyridinyl)-N-phenylurea) at 20 degrees C. 100 g of solvent are used. The solvent is either propylene glycol, propylene carbonate or propylene glycol-n-propyl ether. Only 1.5 g of 6-BA remains soluble in propylene glycol alone. 2.4 g 6-BA remains soluble if 2 g of citric acid is added to propylene glycol. 2.5 g of 6-BA remains soluble if 2 g of tartaric acid is added to propylene glycol. CPPU remains soluble at 7 g, 6 g and 10 g in propylene glycol, propylene carbonate and propylene glycol-n-propyl ether, respectively. Thus, 6-BA solubility is increased by adding citric acid or tartaric acid in propylene glycol. Formulations designated VBC-30001 and ABG-3207 contain 6-BA and Forchlorfenuron, respectively, and citric acid, $C_{12-15}$ alkyl alcohol ethoxylate, propyl gallate and propylene glycol. The weight percent of each component is shown. Storage stability for both formulations (65-022-VB lot for VBC-30001 and 51-004-VB lot for ABG-3207) is high after 12 months at 25 degree C. or 25-40 degree C. tropical conditions. The dilution stability data for both formulations shows that in 342 ppm hard water at about 23 degrees C., 450 ppm of 6-BA 200 ppm of CPPU remain soluble after 24 hr standing.

Low skin, eye, sensitization or inhalation toxicity are shown for ABG-3207 (Category IV) and VBC-30001 (mild skin & eye irritation, Category III). Both formulations employ EPA list 3 or 4 inerts. No flammable IPA nor toxic THFA solvent is used in these studies.

Table 1 also shows a preferred formulation of plant growth regulator compositions of the present invention. Formulation designated VBC-30001 contains 1.93 weight percent of benzyladenine technical (98.5% active ingredient), 2.00 weight percent of citric acid (solubilizer), 4.00 weight percent ethoxylated alcohols (surfactant adjuvant), 0.10 weight percent propyl gallate (antioxidant) and 91.97 weight percent propylene glycol (solvent). A presently preferred composition includes from about 1.5 to about 3.0 weight percent 6-benzyladenine, from about 1.5 to about 3.0 weight percent anhydrous citric acid, from about 3.5 to about 5.5 weight percent ethoxylated alcohols, from about 0.05 to about 0.20 weight percent propyl gallate and from about 91.00 to about 93.00 weight percent propylene glycol. Formulation designated ABG-3207 contains 0.84 weight percent CPPU technical (96.9% active ingredient), 0.5 weight percent anhydrous citric acid, 1.0 weight percent ethoxylated alcohols, and 97.66 weight percent propylene glycol.

Example 3

TABLE 2

Activity improvement: 100-150 ppm 6-BA sprays improved apple thinning/sizing without Carbaryl insecticide (2000 field trials)

| VBC-30001 Rate | Average % Thinning | Average % Increase in Size |
|---|---|---|
| 100 ppm | 25.4 | 18.5 |
| 150 ppm | 29.6 | 18.1 |

Table 2 shows the activity improvement of 100 ppm or 150 ppm 6-BA sprays. Both formulations improved apple thinning and sizing without, SEVIN® (Carbaryl) insecticides as shown in 2000 field trials. In a similar study, better grape sizing using formulation ABG-3207 than other formulations (CPPU technical/IPA) is found.

Example 4

FIG. 1 shows C14 radiolabelled 6-BA uptake from compositions of the present invention (formulation VBC-30001 is designated as "B") in apple leaves, was superior to other compositions designated "A" and "C".

Equal amounts of composition A, B or C (containing radiolabelled 6-BA) were individually applied to apple leaves and the amount uptake was determined from sections of the leaves such as from discs and strips cut from the leaves after a 24 hour period of absorption. A control was also compared to compositions A, B and C. The leaves were rinsed with water and the amount of radiolabelled 6-BA not absorbed in the leaves were determined and quantified (left bar designated "Rinses"). The amount of radiolabelled 6-BA absorbed in the leaves determined from the discs and strips cut from the leaves were determined and quantified (right bar designated "Non-Rinse"). Six trials were taken for each compositions and the control and averaged (except one trial was dropped from "C" and three trials were dropped from "B"). FIG. 1 shows that the 6-BA of the composition of the present invention, "B", was absorbed (Non-Rinse) at a significant higher level compared to that of compositions "A" and "C". The amount of 6-BA of the composition of the present invention that was not absorbed (Rinses) was significantly lower than that of the other compositions.

It is believed that solubilization of the plant growth regulator, such as 6-BA and CPPU, with the organic acid, such as citric acid in conjunction with a surfactant in use dilutions will generate small particle size (microparticles or nanoparticles) for improving uptake or penetration. Small particle size of high dissolution rate is important for activity of water insoluble active ingredients or drugs.

Example 5

Table 3 below shows potential ready-to-mix plant growth formulations which including at least a plant growth regulator, an acid, a surfactant and an antioxidant. Formulation VBC-30009 contains 1.9% 6-BA, 2.0% GA4A7 and 0.45% CPPU. Formulation YW-16-7 contains 4.5% $GA_3$ and 0.42% CPPU. Formulation YW-16-9 contains 2.1% $GA_3$ and 1.9% 6-BA. Formulations YW-26-1 and YW-26-5 contain 2.1% CPPU. Formulation YW-16-4 contains 9% $GA_3$. Additional adjuvants are shown. These formulations show the synergistic effect of combining 6-BA and CPPU with $GA_3$ and $GA_4A_7$ as well as the composition comprises an ethoxylated alkyl alcohol surfactant, organic acid and an antioxidant adjuvants in propylene glycol solvent.

TABLE 3

Ready-to-mix PGR formulations and Combinations

| Ingredients, Wt % | VBC-30009 | YW-16-7 | YW-16-9 | YW-16-4 | YW-26-1 | YW-26-5 |
|---|---|---|---|---|---|---|
| 6-BA tech | 1.9 | | 1.9 | | | |
| CPPU tech | .45 | .42 | | | 2.1 | 2.1 |
| GA4A7 tech | 2.0 | | | | | |
| GA3 tech | | 4.5 | 2.1 | 9.0 | | |
| Citric acid | .5 | .5 | .5 | | 1.0 | 1.0 |
| Propyl gallate | .05 | .1 | .1 | .2 | .05 | .05 |
| Alcohol ethoxylate | | | | | | |
| $C_{12-15}$ | 7.5 | | | | | |
| C11 | | 5.0 | 5.0 | 5.0 | 5.0 | 3.5 |
| Monawet MO-84R2W | | | | | | 1.5 |
| Propylene Glycol UPS | | | | Balance | | |

Adjuvants:
Nonionic surfactants: $C_{12-15}$ and C11 Alkyl alcohol ethoxylates (TOMADOL ® or NEODOL 25-7 and 1-7 ®).
Anionic surfactant: Dioctyl sodium sulfosuccinate (MONAWET MO-84R2W ®)
Antioxidants: Propyl gallate (TENOX PG ®) or Ethoxyquin
Organic acids: Citric, tartaric or glycolic

Example 6

Table 4 below shows stability improvement of formulations containing $GA_4$ and $GA_7$ with ethoxyquin or propyl gallate antioxidant in GA4A7 or GA4A7/6-BA or/and CPPU liquid formulations. Components for the formulations are shown. Storage stability data shows most formulations containing antioxidant have excellent storage stability. Significant stability improvement of GA4 and GA7 were achieved by adding 0.05-0.1% propyl gallate or 0.5% ethoxyquin antioxidant in A % GA4A7 and 6-BA/CPPU plus 2% GA4A7 liquid formulations.

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

TABLE 4

Stability Improvement of GA4A7 Liquid Formulations

| Ingredients, wt % | YW-26-1 | -2 | -3 | -4 | YW-24-1 | -4 | -5 |
|---|---|---|---|---|---|---|---|
| GA4A7 (89.9%) (55-412-CD lot) | 4.5 | 4.5 | 4.5 | 4.5 | 2.0 | 2.0 | 2.0 |
| 6-Benzyladenine (98.5%) | | | | | 1.9 | 1.9 | 1.9 |
| Forchlorfenuron (96.9%) | | | | | .45 | .45 | .45 |
| Citric acid, Anhydrous | | .5 | | | .5 | .5 | .5 |
| Propyl gallate | | | | | | | |
| TENOX SI ® (20% + Citric acid) | | | .5 | | | | |
| TENOX PG ® (99.2%) | | | | | | .05 | .05 |
| Ethoxyquin | | | | | | | |
| Raluquin (96%) | | | | .5 | | | |
| Alcohol ethoxylate | | | | | | | |
| TOMADOL 25-7 ® | | | | | | 7.5 | 5.25 |
| Dioctyl sulfosuccnate | | | | | | | |
| MONAWET MO-84R2W ® (84%) | | | | | | | 2.25 |
| Propylene glycol | | | | Balance | | | |
| Storage Stability: Initial assays (wt %) | | | | | | | |
| GA4 | — | — | — | 2.9 | 1.2 | — | — |
| GA7 | — | — | — | 1.1 | .46 | — | — |
| 8.5 mo. (25-40 C.) | | | | | | | |
| GA4 | 2.56 | 2.60 | 2.81 | 2.87 | 1.04 | 1.27 | 1.26 |
| Remaining | 88% | 90% | 97% | 99% | 83% | 102% | 101% |
| GA7 | .84 | .63 | .89 | 1.03 | .36. | 46 | .45 |
| Remaining | 76% | 57% | 81% | 93% | 77% | 100% | 97% |

We claim:

1. A composition consisting of from about 0.5 to about 2.0 weight percent forchlorfenuron; from about 0.5 to about 2.0 weight percent citric acid; from about 1.0 to about 3.0 weight percent ethoxylated alcohol; and from about 93.0 to about 98.0 weight percent propylene glycol.

2. The composition of claim 1 wherein the ethoxylated alcohol is a $C_{12}$-$C_{15}$ alcohol.

3. A composition consisting of from about 0.5 to about 2.0 weight percent forchlorfenuron; from about 0.5 to about 2.0 weight percent citric acid; from about 1.0 to about 3.0 weight percent ethoxylated alcohol; from about 93.0 to about 98.0 weight percent propylene glycol and an antioxidant.

4. The composition of claim 3 wherein the antioxidant is present in an amount of from about 0.05 to about 0.2 weight percent of the composition.

5. The composition of claim 4 wherein the antioxidant is propyl gallate.

6. A composition consisting of about 0.84 weight percent forchlorfenuron; about 0.5 weight percent citric acid; about 1.0 weight percent ethoxylated $C_{12}$-$C_{15}$ alkyl alcohol; and about 97.66 weight percent propylene glycol.

* * * * *

UNITED STATES PATENT AND TRADEMARK OFFICE
CERTIFICATE OF CORRECTION

| | | |
|---|---|---|
| PATENT NO. | : 7,906,459 B2 | |
| APPLICATION NO. | : 12/565943 | |
| DATED | : March 15, 2011 | |
| INVENTOR(S) | : Wang et al. | |

It is certified that error appears in the above-identified patent and that said Letters Patent is hereby corrected as shown below:

On the Title Page of the patent please replace section (63) with:

--Related U.S. Application Data

(63) Continuation of application No. 11/597,149 filed October 26, 2007, filed as application No. PCT/US2005/017909 on May 23, 2005--

In the specification Column 2, line 6, please delete "($GA_{4+7}$)" and replace it with --($GA_4A_7$)--

In the specification Column 2, line 30, please delete "GA4+A7" and replace it with --$GA_4A_7$--

In the specification Column 2, line 32, please delete "GA4+A7" and replace it with --$GA_4A_7$--

In the specification Column 4, lines 10-11, please delete "6-benzyl adenine" and replace it with --6-benzyladenine--

In the specification Column 4, line 50, please delete "gibberelin" and replace it with --gibberellin--

In the specification Column 4, line 51, please delete "6-benzyl adenine" and replace it with --6-benzyladenine--

In the specification Column 6, line 3, please delete "in" and replace it with --In--

In the specification Column 6, line 35, please delete "91-60" and replace it with --91-6®--

In the specification Column 6, line 59, please delete "GA3 or GA4A7" and replace it with --$GA_3$ or $GA_4A_7$--

Signed and Sealed this
Twenty-first Day of June, 2011

David J. Kappos
*Director of the United States Patent and Trademark Office*

In the specification Column 7, line 47, please delete "fruit is" and replace it with --fruit that is--

In the specification Column 8, line 3, please delete "Blugrass (*Poe compressa L.*) and replace it with --Bluegrass (*Poa compressa L.*)--